United States Patent [19]

Julia

[11] Patent Number: 4,968,844

[45] Date of Patent: Nov. 6, 1990

[54] PROCESS FOR PREPARING RETINAL

[75] Inventor: Marc Julia, Paris, France

[73] Assignee: Centre National de la Recherche Scientifique (C. N. R. S.), Paris, France

[21] Appl. No.: 263,018

[22] Filed: Oct. 27, 1988

[30] Foreign Application Priority Data

Oct. 29, 1987 [FR] France ................... 8714980

[51] Int. Cl.$^5$ ............................. C07C 33/02
[52] U.S. Cl. ......................... 568/39; 568/41;
546/301; 548/169; 548/170; 548/209; 548/213;
548/186; 548/187; 548/221; 548/241; 548/229;
548/324
[58] Field of Search ............... 546/301; 548/170, 187,
548/209, 213, 221, 241, 324, 229, 169, 186;
568/41,39

[56] References Cited

PUBLICATIONS

March, J. *Advanced Organic Chemistry*, 3rd. ed. Wiley & Sons (1987). pp. 329-30, 413-14.
Lowy, A. and Harrow, B. *An Intro. to Organic Chemistry*, 7th ed. Wiley & Sons (1951). p. 215.

*Primary Examiner*—Mary C. Lee
*Assistant Examiner*—Zinna Northington-Davis
*Attorney, Agent, or Firm*—Stevens, Davis, Miller & Mosher

[57] ABSTRACT

Retinal is prepared by condensing a $C_{15}$ sulphide of formula:

in which $R_1$ denotes aryl, aralkyl, pyridyl, 2-thiazolyl, 2-benzothiazolyl, 2-benzimidazolyl or 2-benzoxazolyl, with a haloacetal of formula:

in which X denotes a halogen atom and R denotes an alkyl radical containing 1 to 4 carbon atoms, to give a $C_{20}$ sulphide acetal of formula:

in which $R_1$ and R are defined as above, hydrolysing the said sulphide acetal to give a $C_{20}$ sulphide aldehyde of formula:

in which $R_1$ is defined as above, desulphurizing the said sulphide aldehyde to give retinal, and isolating the retinal obtained.

11 Claims, No Drawings

PROCESS FOR PREPARING RETINAL

The present invention relates to the preparation of rental of formula:

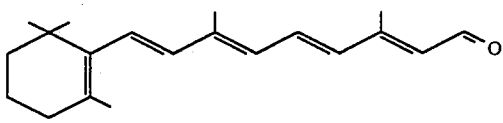
(I)

which is an intermediate in vitamin A synthesis, optionally in the form of an acetate.

It is known to prepare retinal by condensing a $C_{15}$ sulphone of general formula:

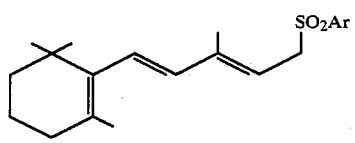
(II)

in which Ar denotes an optionally substituted phenyl radical, with a $C_5$ haloacetal of general formula:

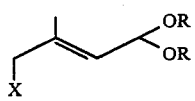
(III)

in which X denotes a halogen (chlorine, bromine) atom and R denotes an alkyl radical containing 1 to 4 carbon atoms (preferably a methyl or ethyl radical), followed by the hydrolysis and desulphonation of the $C_{20}$ sulphone acetal of general formula:

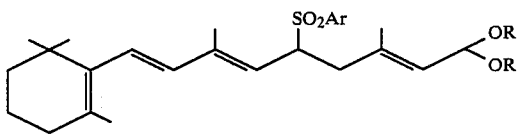
(IV)

in which Ar and R are defined as above. However, while this process gives satisfactory results, it requires for its implementation, especially for the preparation of the $C_{15}$ sulphone of general formula (II), the use of an arylsulphinate whose preparation and recovery involve lengthy and expensive techniques.

It has now been found, and this forms the subject of the present invention, that retinal, containing a proportion of all-trans isomer generally greater than 70%, may be obtained in good yield by a process which comprises condensing a $C_{15}$ sulphide of formula:

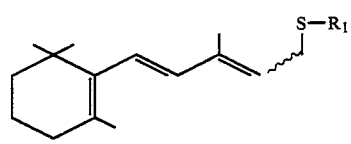
(V)

in which $R_1$ denotes aryl, preferably optionally substituted phenyl, aralkyl, preferably benzyl, pyridyl, 2-thiazolyl, 2-benzothiazolyl, 2-benzimidazolyl or 2-benzoxazolyl, with a haloacetal of formula (III), in which X and R are as herein-before defined, to give a $C_{20}$ sulphide acetal of formula:

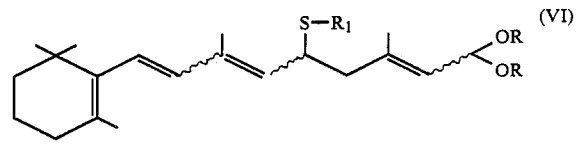
(VI)

in which $R_1$ and R are defined as above, hydrolysing the said sulphide acetal to give a $C_{20}$ sulphide aldehyde of formula:

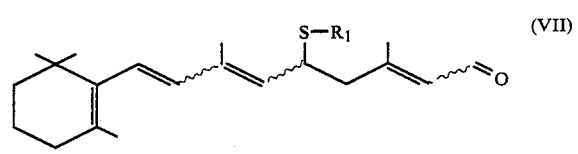
(VII)

in which $R_1$ is defined as above, desulphurizing the said sulphide aldehyde to give retinal and isolating the retinal obtained.

The condensation of the $C_{15}$ sulphide of formula (V) with the haloacetal of formula (III) can generally be performed in the presence of a basic agent, which is necessary in order to produce anionization of the sulphide. Basic agents which are especially suitable include alkali metal hydroxides, alcoholates, hydrides or amides, and organometallic compounds such as organozinc, organolithium or organomagnesium compounds. They can be used alone or in combination with another basic agent whose purpose is to neutralize the hydracid formed.

The reaction is generally performed at a temperature between $-100°$ and $100°$ C.

The reaction may be carried out in an organic solvent which may be an aliphatic hydrocarbon (hexane), aromatic hydrocarbon (benzene, toluene), alcohol (methanol, ethanol), ether (diethyl ether, dioxane, tetrahydrofuran), amide (dimethylformamide, dimethylacetamide), dimethyl sulphoxide, N-methylpyrrolidone or hexamethylphosphotriamide.

For example the condensation may be performed in the presence of butyllithium and diazabicyclooctane, working in tetrahydrofuran at a temperature in the region of $-30°$ C.

The sulphide acetal of formula (VI) may be converted to the sulphide aldehyde of formula (VII) by hydrolysis in an acid medium. For example, the hydrolysis may be carried out in the presence of oxalic acid at a temperature in the region of $20°$ C.

The desulphurization of the sulphide aldehyde of formula (VII) may be accomplished by treatment with an inorganic or organic basic agent such as an alkali metal hydroxide, an alkali metal carbonate or an alkali metal alcoholate. For example, the desulphurization may be carried out at a temperature in the region of $20°$ C. using sodium methylate in methanol or sodium ethylate in ethanol.

The process according to the invention enables retinal to be obtained from the $C_{15}$ sulphide in yields generally greater than 75%.

Depending on the stereoisomerism of the $C_{15}$ sulphide of formula (V) and of the haloacetal of formula (III), the $C_{20}$ sulphide acetal of formula (VI), as well as the $C_{20}$ sulphide aldehyde of formula (VII), is most often obtained in the form of a mixture of stereoisomers. Irrespective of the composition of the mixture, the process according to the invention enables a mixture of retinals to be obtained in which the all-trans isomer represents 70%.

The retinal obtained according to the process of the present invention may be converted to vitamin A by the application of known methods.

The $C_{15}$ sulphides of formula (V) may be obtained by the action of a thiol on vinyl-$\beta$-ionol in the presence of a catalytic amount of a strong acid. For example, the $C_{15}$ sulphide of formula (V) in which $R_1$ denotes a phenyl radical may be obtained by the action of thiophenol on vinyl-$\beta$-ionol in the presence of fluorosulphonic acid, working in nitromethane at a temperature in the region of 0° C.

The e ample which follows illustrates the invention.

EXAMPLE (1) 4.5 g of $C_{15}$ phenyl sulphide (E/Z=70:30) (13.6 mmol) and 1.84 g of diazabicyclooctane (16.3 mmol) are dissolved under an argon atmosphere in 40 cm³ of anhydrous tetrahydrofuran.

11 cm³ of a 1.48 N solution of n-butyllithium in hexane are added dropwise in the course of 15 minutes, followed, in the course of 10 minutes, by 3.10 g of $C_5$ dimethyl chloroacetal (E/Z=75:25) assaying at 87% (16 mmol), the temperature being maintained at −30° C.

The dark red reaction mixture gradually decolourizes and becomes orange-yellow. It is stirred for 1 hour at −30° C, and the temperature is then allowed to rise to around 20° C. 1 g of ammonium chloride is then added and the mixture is left to stand overnight at a temperature between 18° and 20° C.

After evaporation of the tetrahydrofuran at 20° C. under reduced pressure, the oily residue is taken up with ether (30 cm³), and an acetic acid/water mixture (50:50 by volume) is then added until the pH is in the region of 7, followed immediately by saturated aqueous sodium bicarbonate solution (30 cm³) and saturated sodium chloride solution (30 cm³).

After settling has taken place, the organic phases are separated off and dried over sodium sulphate. After filtration and evaporation of the solvent under reduced pressure, 6.20 g of a pale yellow oil are obtained, and this is purified by chromatography on activated neutral alumina, eluting with 1 liter of pentane, followed by 1 liter of pentane containing 1% of ethyl ether, and then by 2 liters of pentane containing 2% of ethyl ether.

1.2 g of dimethyl $C_{20}$ phenyl sulphide acetal (7E, 9E, 13E) and 3.95 g of a dimethyl $C_{20}$ phenyl sulphide acetal mixture (7E, 9E, 13E; 7E, 9E, 13Z; 7E, 9Z, 13E and 7E, 9Z, 13Z) are thereby obtained.

The yield is in the region of 85%.

(2) 0.3 cm³ of a 10% strength aqueous oxalic acid solution is added to a suspension of 3 g of silica (MERCK silica) in 5 cm³ of methylene chloride, followed, while the mixture is shielded from the light and kept under an argon atmosphere, by 1 g of dimethyl $C_{20}$ phenyl sulphide acetal.

After 15 minutes at a temperature in the region of 20° C., the reaction is complete. The mixture is diluted by adding 3 cm³ of methylene chloride and then filtered on no.4 sintered lass under a nitrogen atmosphere. The silica is washed with 3 times 5 cm³ of methylene chloride. The organic phases are dried over sodium sulphate. After filtration and evaporation of the solvent under reduced pressure at 15° C., 0.855 g of $C_{20}$ phenyl sulphide aldehyde is obtained.

The yield is 95%.

(3) 2 cm³ of a 1 N solution of sodium ethylate in ethanol are added at 20° C. to 0.788 g of $C_{20}$ phenyl sulphide aldehyde dissolved in 2 cm³ of absolute ethanol while the mixture is kept under an argon atmosphere and shielded from the light. After 15 minutes, 10 cm³ of water and 10 cm³ of methylene chloride are added. After settling has taken place, the organic phase is separated off, washed with saturated sodium chloride solution until the pH=7, and then dried over sodium sulphate. After filtration and evaporation of the solvent, while the solution is kept under an argon atmosphere and shielded from the light, 547 mg of an oil, which consists of 70% of all-trans-retinal, 8% of 9-cis isomer, 20% of 13-cis isomer and 2% of di-cis isomer, are obtained.

The yield is 96%.

I claim:

1. Process for preparing retinal with an all trans content of about 70%, which comprises condensing a $C_{15}$ sulphide (E/Z=70:30) of the formula:

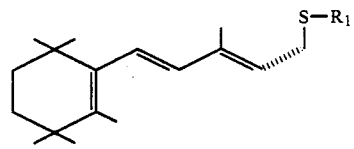

in which $R_1$ denotes phenyl, benzyl, pyridyl, 2-thiazolyl, 2-benzothiazolyl, 2-benzimidazolyl or 2-benzoxazolyl, with haloacetal (E/Z=75:25) of the formula:

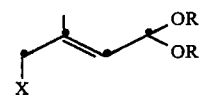

in which X denotes halogen and R denotes alkyl containing 1 to 4 carbon atoms, to give a $C_{20}$ sulphide acetal of the formula: S-$R_1$ OR

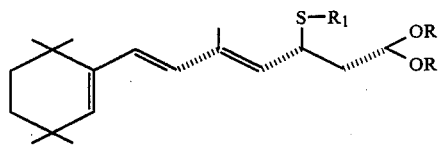

in which $R_1$ and R are defined as above,
   hydrolyzing the sulphide acetal to give a $C_{20}$ sulphide aldehyde of the formula:

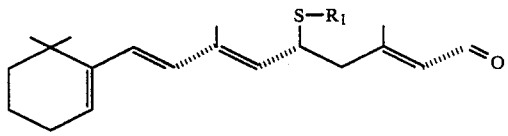

in which $R_1$ is defined as above,
   desulphurizing the sulphide aldehyde to give retinal with an all trans content of about 70%, and
   isolating the retinal obtained.

2. Process according to claim 1, in which the condensation of the $C_{15}$ sulphide with the $C_5$ haloacetal is performed in the presence of a basic agent, with or without a second basic agent to neutralize the hydracid formed, in an organic solvent at a temperature between $-100°$ and $100°$ C.

3. Process according to claim 2, in which the basic agent is an alkali metal hydroxide, alcoholate, hydride or amide or an organozinc, organolithium or organomagnesium derivative.

4. Process according to claim 2, in which the solvent is an aliphatic hydrocarbon, aromatic hydrocarbon, alcohol, ether, amide, dimethyl sulphoxide, N-methylpyrrolidone or hexamethylphosphotriamide.

5. Process according to claim 1, in which the hydrolysis of the $C_{20}$ sulphide acetal is performed in an acid medium.

6. Process according to claim 1, in which the desulphurization of the $C_{20}$ sulphide aldehyde is accomplished by means of an inorganic or organic basic agent which is an alkali metal hydroxide, carbonate or alcoholate.

7. Process according to claim 1 in which $R_1$ is phenyl, X is chlorine and R is methyl.

8. A $C_{20}$ sulphide acetal of formula:

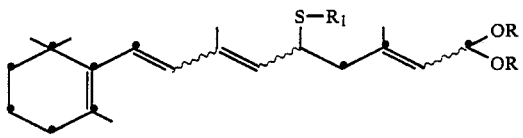

in which $R_1$ denotes an phenyl, benzyl, pyridyl, 2-thiazolyl, 2-benzothiazolyl, 2-benzimidazolyl or 2-benzoxazolyl radical and R denotes an alkyl radical containing 1 to 4 carbon atoms.

9. The $C_{20}$ sulphide acetal according to claim 8 in which $R_1$ phenyl and R is methyl.

10. The $C_{20}$ sulphide aldehyde of formula:

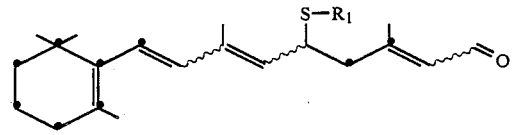

in which $R_1$ denotes an phenyl, benzyl, pyridyl, 2-thiazolyl, 2-benzothiazolyl, 2-benzimidazolyl or 2-benzoxazolyl radical.

11. The $C_{20}$ sulphide aldehyde according to claim 10 in which $R_1$ is phenyl.

* * * * *